United States Patent [19]

Becker et al.

[11] Patent Number: 5,236,933

[45] Date of Patent: Aug. 17, 1993

[54] USE OF A COMBINATION OF ANGIOTENSIN-CONVERTING ENZYME INHIBITOR AND CALCIUM ANTAGONIST FOR THE TREATMENT OF PROTEINURIA

[75] Inventors: Reinhard Becker, Wiesbaden; Rainer Henning, Hattersheim am Main; Volker Teetz, Hofheim am Taunus; Hansjörg Urbach, Kronberg, all of Fed. Rep. of Germany

[73] Assignee: Hoechst Aktiengesellschaft, Frankfurt am Main, Fed. Rep. of Germany

[21] Appl. No.: 798,501

[22] Filed: Nov. 26, 1991

[30] Foreign Application Priority Data

Nov. 27, 1990 [DE] Fed. Rep. of Germany ....... 4037691

[51] Int. Cl.$^5$ ............... A61K 31/47; A61K 31/44; A61K 31/40
[52] U.S. Cl. ................... 514/307; 514/356; 514/412; 514/423
[58] Field of Search ............ 514/307, 356, 412, 423

[56] References Cited

U.S. PATENT DOCUMENTS

| | | | |
|---|---|---|---|
| 4,129,571 | 12/1978 | Ondetti et al. | 260/326.2 |
| 4,154,960 | 5/1979 | Ondetti et al. | 562/426 |
| 4,294,832 | 9/1981 | Yoneda et al. | 424/258 |
| 4,344,949 | 8/1982 | Hoefle et al. | 424/258 |
| 4,350,633 | 9/1982 | Kim et al. | 260/326.11 |
| 4,350,704 | 9/1982 | Hoefle et al. | 424/274.2 |
| 4,374,829 | 2/1983 | Harris et al. | 424/177 |
| 4,374,847 | 2/1983 | Gruenfield | 424/274 |
| 4,454,292 | 6/1984 | Kim et al. | 548/491 |
| 4,470,972 | 9/1984 | Gold et al. | 424/177 |
| 4,703,038 | 10/1987 | Garthoff et al. | 514/19 |
| 5,098,910 | 3/1992 | Becker et al. | 514/299 |

FOREIGN PATENT DOCUMENTS

| | | |
|---|---|---|
| 0065301 | 11/1982 | European Pat. Off. . |
| 0079522 | 5/1983 | European Pat. Off. . |
| 0052991 | 2/1987 | European Pat. Off. . |
| 0381075 | 8/1990 | European Pat. Off. . |

OTHER PUBLICATIONS

CA 114(5):35665v, Tolins et al. (1990).
T Unger, et al., Handbook of Experimental Pharmacology, vol. 93, pp. 379-481 (1989).
Journal of Cardiovascular Pharmacology, vol. 16, No. 6, (Dec. 1990), pp. 924-930, H. J. Kloke et al.
Journal of Cardiovascular Pharmacology, vol. 10, No. S10, (1987), pp. 167-169, B. Jackson et al.
AM. Heart Journal, vol. 116, No. 6/1, (1988), pp. 1591-1606, J. B. Kostis.
Z. Kardiol., vol. 77, No. S3, (1988), pp. 73-88, D. Klaus.

Primary Examiner—Frederick E. Waddell
Assistant Examiner—Kimberly R. Jordan
Attorney, Agent, or Firm—Finnegan, Henderson, Farabow, Garrett & Dunner

[57] ABSTRACT

The invention relates to the prevention and therapy of proteinuria by administration of a combination of ACE inhibitor and calcium antagonist.

4 Claims, 4 Drawing Sheets

USE OF A COMBINATION OF ANGIOTENSIN-CONVERTING ENZYME INHIBITOR AND CALCIUM ANTAGONIST FOR THE TREATMENT OF PROTEINURIA

DESCRIPTION

The present invention relates to the prevention and therapy of proteinuria by combined administration of an angiotensin-converting enzyme inhibitor (ACE inhibitor) and of a calcium antagonist.

ACE inhibitors are compounds which prevent the conversion of angiotensin I into the pressor-active angiotensin II. Such compounds are described, for example, in the following patent applications or patents: U.S. Pat. Nos. 4,350,633, 4,344,949, 4,294,832, 4,350,704, EP-A 31,741, EP-A 51,020, EP-A 49,658, EP-A 29,488, EP-A 46,953, EP-A 52,870, U.S. Pat. Nos. 4,129,571, 4,154,960, 4,374,829, EP-A 79522, EP-A 79022, EP-A 51301, U.S. Pat. Nos. 4,454,292, 4,374,847, EP-A 72352, EP-A 84164, U.S. Pat. No. 4,470,972, EP-A-65301 and EP-A-52991. Their hypotensive action is well documented.

Calcium antagonists are those compounds which affect the inflow of calcium ions into cells, in particular smooth muscle cells. Such compounds and their hypotensive action are set down in a multiplicity of publications and patent applications.

Combinations of ACE inhibitors and calcium antagonists and their use in the treatment of high blood pressure are known, for example, from EP-A-180,785 and EP-A-265,685.

Proteinuria occurs, in particular, in diseases of the renal tissue (nephritis, nephrosis, contracted kidney) and in engorged kidney as a result of cardiac insufficiency; in addition to the albumins, the globulins and other blood protein bodies also pass into the urine. The highest orders of proteinuria are found in nephrosis and amyloidosis. Constant proteinuria in diabetes mellitus points to the development of glomerulosclerosis (Kimmelstiel-Wilson's syndrome).

It has now surprisingly been found that a combination of ACE inhibitor and calcium antagonist is suitable for the prevention and therapy of proteinuria, as can typically occur in diabetes mellitus and kidney weight loss (donor kidney), but also as a secondary phenomenon of glomerulosclerosis as a result of hyperperfusion of the glomeruli. Orally active ACE inhibitors are advantageous, such as, for example, ramipril, enalapril, captopril, alacepril, benazepril, ceranapril, cilazapril, delapril, fosinopril, imidapril, libenzapril, lisinopril, moexipril, moveltipril, perindopril, quinapril, spirapril, zofenopril, trandolapril, BPL 36378, CS 622, FPL 63547, S 9650 and others. Orally active ACE inhibitors are described, for example, in "Pharmacology of Antihypertensive Therapeutics" (Eds. D. Ganten, P. J. Mutrow) Springer Verlag, Berlin 1990, pp. 377–480.

Suitable ACE inhibitors are in particular the following compounds of the formula I or their physiologically tolerable salts:

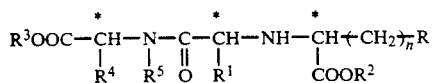

in which
n=1 or 2,
R=hydrogen,
an optionally substituted aliphatic radical having 1-8 carbon atoms,
an optionally substituted alicyclic radical having 3-9 carbon atoms,
an optionally substituted aromatic radical having 6-12 carbon atoms,
an optionally substituted araliphatic radical having 7-14 carbon atoms,
an optionally substituted alicyclic-aliphatic radical having 7-14 carbon atoms,
a radical $OR^a$ or $SR^a$, in which
$R^a$ is an optionally substituted aliphatic radical having 1-4 carbon atoms, an optionally substituted aromatic radical having 6-12 carbon atoms or an optionally substituted heteroaromatic radical having 5-12 ring atoms,
$R^1$ is hydrogen,
an optionally substituted aliphatic radical having 1-6 carbon atoms,
an optionally substituted alicyclic radical having 3-9 carbon atoms,
an optionally substituted alicyclic-aliphatic radical having 4-13 carbon atoms,
an optionally substituted aromatic radical having 6-12 carbon atoms,
an optionally substituted araliphatic radical having 7-16 carbon atoms,
an optionally substituted heteroaromatic radical having 5-12 ring atoms or the side chain, which is protected if necessary, of a naturally occurring α-amino acid,
$R^2$ and $R^3$ are identical or different and are hydrogen,
an optionally substituted aliphatic radical having 1-6 carbon atoms,
an optionally substituted alicyclic radical having 3-9 carbon atoms,
an optionally substituted aromatic radical having 6-12 carbon atoms,
an optionally substituted araliphatic radical having 7-16 carbon atoms and
$R^4$ and $R^5$, together with the atoms carrying them, form a heterocyclic, mono-, bi- or tricyclic ring system having 3 to 15 carbon atoms, suitable ring systems of this type in particular being those of the following series:
tetrahydroisoquinoline (A); decahydroisoquinoline (B); octahydroindole (C); octahydrocyclopenta[b]pyrrole (D); 2-azaspiro[4.5]decane (E); 2-azaspiro[4.4]nonane (F); spiro[(bicyclo[2.2.1]heptane)-2,3-pyrrolilidine] (G); spiro[(bicyclo[2.2.2]octane)-2,3-pyrrolidine] (J); 2-azatricyclo[4,3,0,1$^{6,9}$]decane (I); decahydrocyclohepta[b]pyrrole (J); octahydroisoindole (K); octahydrocyclopenta[c]pyrrole (L); 2,3,3a,4,5,7a-hexahydroindole (M); 2-azabicyclo[3.1.0]hexane (N); hexahydrocyclopenta[b]pyrrole (O); pyrrolidine (P); thiazolidine (Q); which can all be optionally substituted. However, the unsubstituted systems which have the following structural formulae are preferred.

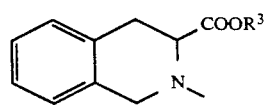

-continued

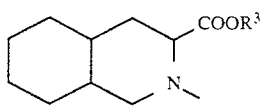  B

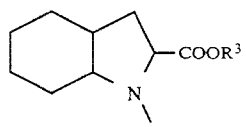  C

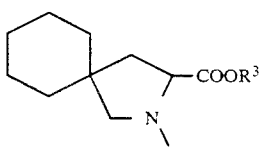  E

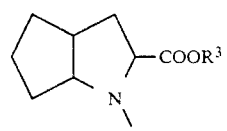  D

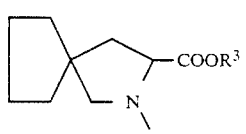  F

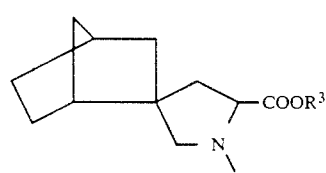  G

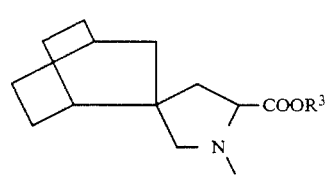  H

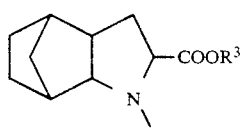  I

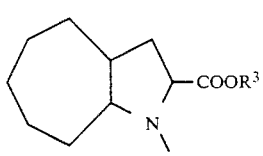  J

-continued

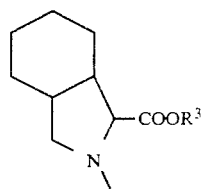  K

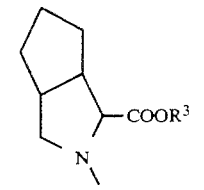  L

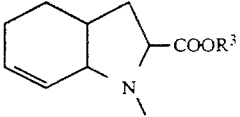  M

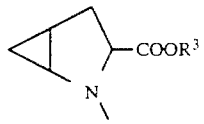  N

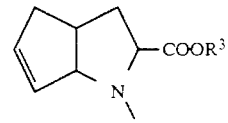  O

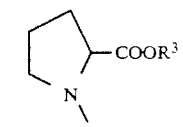  P

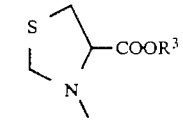  Q

In the compounds which have several chiral atoms, all possible diastereomers, or mixtures of various diastereomers, are possible as racemates or enantiomers. The S-configuration of the carbon atoms marked with a star is preferred.

Preferred ACE inhibitors are those of the formula I in which n=1 or 2,
R is hydrogen,
  alkyl having 1-8 carbon atoms,
  alkenyl having 2-6 carbon atoms,
  cycloalkyl having 3-9 carbon atoms,
  aryl having 6-12 carbon atoms,
  which can be mono-, di- or trisubstituted by ($C_1$–$C_4$)-alkyl, ($C_1$–$C_4$)-alkoxy, hydroxyl, halogen, nitro, amino, aminoethyl or ($C_1$–$C_4$)-alkylamino, alkoxy having 1-4 carbon atoms,
aryloxy having 6-12 carbon atoms,
which can be substituted as described above for aryl,
mono- or bicyclic heteroaryloxy having 5-7 carbon atoms and 8-10 ring atoms, of which 1 or 2 ring atoms are sulfur or oxygen atoms and/or 1 to 4 ring atoms are nitrogen,
which can be substituted as described above for aryl,
amino-($C_1$-$C_4$)-alkyl
($C_1$-$C_4$)-alkanoylamino-($C_1$-$C_4$)-alkyl,
($C_7$-$C_{13}$)-aroylamino-($C_1$-$C_4$)-alkyl,
($C_1$-$C_4$-alkoxy-carbonylamino-($C_1$-$C_4$)-alkyl,
($C_6$-$C_{12}$)-aryl-($C_1$-$C_4$)-alkoxycarbonylamino-($C_1$-$C_4$)-alkyl,
($C_1$-$C_4$)-alkylamino-($C_1$-$C_4$)-alkyl,
di-($C_1$-$C_4$)-alkylamino-($C_1$-$C_4$)-alkyl,
guanidino-($C_1$-$C_4$)-alkyl,
imidazolyl, indolyl,
($C_1$-$C_4$)-alkylthio,
($C_1$-$C_4$)-alkylthio-($C_1$-$C_4$)-alkyl,
($C_6$-$C_{12}$)-arylthio-($C_1$-$C_4$)-alkyl,
which can be substituted in the aryl moiety as described above for aryl,
($C_6$-$C_{12}$)-aryl-($C_1$-$C_4$)-alkylthio,
which can be substituted in the aryl moiety as described above for aryl,
carboxy-($C_1$-$C_4$)-alkyl,
carboxyl, carbamoyl,
carbamoyl-($C_1$-$C_4$)-alkyl,
($C_1$-$C_4$)-alkoxy-carbonyl-($C_1$-$C_4$)-alkyl,
($C_6$-$C_{12}$)-aryloxy-($C_1$-$C_4$)-alkyl,
which can be substituted in the aryl moiety as described above for aryl or
($C_6$-$C_{12}$)-aryl($C_1$-$C_4$)-alkoxy,
which can be substituted in the aryl moiety as described above for aryl,
$R^1$ is hydrogen,
alkyl having 1-6 carbon atoms,
alkenyl having 2-6 carbon atoms,
alkynyl having 2-6 carbon atoms,
cycloalkyl having 3-9 carbon atoms,
cycloalkenyl having 5-9 carbon atoms,
($C_3$-$C_9$)-cycloalkyl-($C_1$-$C_4$)-alkyl,
($C_5$-$C_9$)-cycloalkenyl-($C_1$-$C_4$)-alkyl,
optionally partially hydrogenated aryl having 6-12 carbon atoms, which can be substituted as described above for R,
($C_6$-$C_{12}$)-aryl-($C_1$-$C_4$)-alkyl or ($C_7$-$C_{13}$)-aroyl-($C_1$ or $C_2$)-alkyl,
which can both be substituted like the above aryl, mono- or bicyclic, optionally partially hydrogenated heteroaryl having 5-7 carbon atoms and 8-10 ring atoms, of which 1 or 2 ring atoms are sulfur or oxygen atoms and/or 1 to 4 ring atoms are nitrogen atoms, which can be substituted like the above aryl or is the optionally protected side chain of a naturally occurring α-amino acid $R^1$—CH(NH$_2$)—COOH,
$R^2$ and $R^3$ are identical or different and are hydrogen, alkyl having 1-6 carbon atoms,
alkenyl having 2-6 carbon atoms,
di-($C_1$-$C_4$)-alkylamino-($C_1$-$C_4$)-alkyl,
($C_1$-$C_5$)-alkanoyloxy-($C_1$-$C_4$)-alkyl,
($C_1$-$C_6$)-alkoxy-carbonyloxy-($C_1$-$C_4$)-alkyl,
($C_7$-$C_{13}$)-aryloxy-($C_1$-$C_4$)-alkyl,
($C_6$-$C_{12}$)-aryloxycarbonyloxy-($C_1$-$C_4$)-alkyl,
aryl having 6-12 carbon atoms,
($C_6$-$C_{12}$))-aryl-($C_1$-$C_4$)-alkyl, ($C_3$-$C_9$)-cycloalkyl or
($C_3$-$C_9$)-cycloalkyl-($C_1$-$C_4$)-alkyl and
$R^4$ and $R^5$ have the abovementioned meaning,
and very particularly preferred compounds are those of the formula I in which
n=1 or 2,
R is ($C_1$-$C_6$)-alkyl, ($C_2$-$C_6$)-alkenyl, ($C_3$-$C_9$)-cycloalkyl, amino-($C_1$-$C_4$)-alkyl, ($C_2$-$C_5$)-acylamino-($C_1$-$C_4$)-alkyl, ($C_7$-$C_{13}$)-aroylamino-($C_1$-$C_4$)-alkyl, ($C_1$-$C_4$)-alkoxycarbonylamino-($C_1$-$C_4$)-alkyl, ($C_6$-$C_{12}$)-aryl-($C_1$-$C_4$)-alkoxycarbonylamino-($C_1$-$C_4$)-alkyl, ($C_6$-$C_{12}$)-aryl, which can be mono-, di- or trisubstituted by ($C_1$-$C_4$)-alkyl, ($C_1$-$C_4$)-alkoxy, hydroxyl, halogen, nitro, amino, ($C_1$-$C_4$)-alkylamino, di-($C_1$-$C_4$)-alkylamino and/or methylenedioxy, or 3-indolyl, in particular methyl, ethyl, cyclohexyl, tertbutoxycarbonylamino-($C_1$-$C_4$)-alkyl, benzoyloxycarbonylamino-($C_1$-$C_4$)-alkyl or phenyl, which can be mono- or disubstituted or, in the case of methoxy, trisubstituted by phenyl, ($C_1$-$C_2$)-alkyl, ($C_1$ or $C_2$)-alkoxy, hydroxyl, fluorine, chlorine, bromine, amino, ($C_1$-$C_4$)-alkylamino, di-($C_1$-$C_4$)alkylamino, nitro and/or methylenedioxy,
$R^1$ is hydrogen or ($C_1$-$C_6$)-alkyl which can optionally be substituted by amino, ($C_1$-$C_6$)-acylamino or benzoylamino, ($C_2$-$C_6$)-alkenyl, ($C_3$-$C_9$)-cycloalkyl, ($C_5$-$C_9$)-cycloalkenyl, ($C_3$-$C_7$)-cycloalkyl-($C_1$-$C_4$)-alkyl, ($C_6$-$C_{12}$)-aryl or partially hydrogenated aryl which in each case can be substituted by ($C_1$-$C_4$)-alkyl, ($C_1$ or $C_2$)-alkoxy or halogen, ($C_6$-$C_{12}$)-aryl-($C_1$ to $C_4$)-alkyl or ($C_7$-$C_{13}$)-aroyl-($C_1$-$C_2$)-alkyl, which can both be substituted in the aryl radical as defined above, a mono- or bicyclic heterocyclic radical having 5 to 7 carbon atoms and 8 to 10 ring atoms, of which 1 or 2 ring atoms are sulfur or oxygen atoms and/or 1 to 4 ring atoms are nitrogen atoms, or a side chain of a naturally occurring, optionally protected α-amino acid, but in particular hydrogen,($C_1$-$C_4$)-alkyl, ($C_2$ or $C_3$)-alkenyl, the optionally protected side chain of lysine, benzyl, 4-methoxybenzyl, 4-ethoxybenzyl, phenethyl, 4-aminobutyl or benzoylmethyl,
$R^2$ and $R^3$ are identical or different hydrogen, ($C_1$-$C_6$)-alkyl, ($C_2$-$C_6$)-alkenyl or ($C_6$-$C_{12}$))-aryl-($C_1$-$C_4$)-alkyl radicals, but in particular hydrogen, ($C_1$-$C_4$)-alkyl or benzyl and
$R^4$ and $R^5$ have the abovementioned meaning.
$R^4$ and $R^5$ are preferably together a radical of the formula

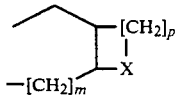

in which m=0 or 1, p=0, 1 or 2 and X=—CH$_2$—, —CH$_2$—CH$_2$— or —CH=CH—, where a 6-membered ring formed with X can also be a benzene ring.
Aryl here as in the following is preferably understood as meaning optionally substituted phenyl, biphenylyl or naphthyl. The same applies to radicals derived from aryl, such as aryloxy and arylthio. Aroyl is in particular understood as meaning benzoyl. Aliphatic radicals can be straight-chain or branched.
A mono- or bicyclic heterocyclic radical having 5 to 7 carbon atoms and 8 to 10 ring atoms, of which 1 or 2 ring atoms are sulfur or oxygen atoms and/or of which 1 to 4 ring atoms are nitrogen atoms, is understood as meaning, for example, thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. These radicals can also be partially or completely hydrogenated. Naturally occurring α-amino acids are described, for example, in Houben-Weyl, Methoden der Organischen Chemie, (Methods of Organic Chemistry), Vol. XV/1 and XV/2.

If $R^1$ is a side chain of a protected naturally occurring α-amino acid, such as, for example, protected Ser, Thr, Asp, Asn, Glu, Arg, Lys, Hyl, Cys, Orn, Cit, Tyr, Trp, His or Hyp, preferred protective groups are those customary in peptide chemistry (cf. Houben-Weyl, Vol. XV/1 and XV/2). If R is the protected lysine side chain, the known amino protective groups, but in particular Z, Boc or $(C_1-C_6)$-alkyl, in particular methyl or ethyl, are suitable.

Particularly preferred compounds are 2-[N-(1-S-ethoxycarbonyl-3-phenylpropyl)-S-alanyl]-(1S,3S,5S)-2-azabicyclo[3.3.0]octane-3-carboxylic acid (ramipril), 1-[N-(1-S-ethoxycarbonyl-3-phenylpropyl)-S-alanyl]-(2S,3aR,7aS)-octahydro[1H] indole-2-carboxylic acid (trandolapril), 2-(N-1-S-ethoxycarbonyl-3-phenylpropyl)-S-alanyl]-1,2,3,4-tetrahydroisoquinoline-3-S-carboxylic acid (quinapril), 1-[N-(1-S-ethoxycarbonyl-3-phenylpropyl)-S-alanyl]-S-proline (enalapril), 1-[N-(1-S-ethoxycarbonyl-3-phenylpropyl)-S-lysyl]-S-proline (lisinopril), 1-[N-(1-S-ethoxycarbonyl-n-butyl]-S-alanyl]-(2S,3aS,7aS)-octahydro[1H]indole-2-carboxylic acid (perindopril) and the corresponding dicarboxylic acids. Orally active ACE inhibitors, such as, for example, ramipril, enalapril, captopril, alacepril, benazepril, ceranapril, cilazapril, delapril, fosinopril, imidazpril, libenzapril, lisinopril, moexipril, moveltipril, perindopril, quinapril, spirapril, zofenopril, trandolapril, BPL 36378, CS 622, FPL 63547, S 9650 and others are advantageous.

The compounds of the formula I according to the invention can be prepared, for example, by reacting compounds of the formula V with compounds of the formula VI

The reaction of these compounds can be carried out, for example, in analogy to known peptide coupling processes in an organic solvent such as DMF, $CH_2Cl_2$, DMA in the presence of coupling auxiliaries, such as carbodiimides (for example dicyclohexylcarbodiimide), diphenylphosphoryl azide, alkanephosphonic anhydrides, dialkylphosphinic anhydrides or N,N-succinimidyl carbonates in a solvent such as $CH_3CN$. Amino groups in compounds of the formula V can be activated with tetraethyl disphosphite. The compounds of the formula VI can be converted into active esters (for example with 1-hydroxybenzotriazole), mixed anhydrides (for example with chloroformic acid esters), azides or carbodiimide derivatives and thus activated (cf. Schröder, Lübke, The Peptides, Volume 1, New York 1965, pages 76-136). The reaction is preferably carried out between −20° C. and the boiling point of the reaction mixture.

Likewise, compounds of the formula VII can be reacted with compounds of the formula VIII with the formation of compounds of the formula I.

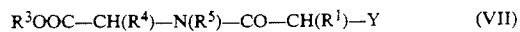

in which either $Y^1$ is amino and $Y^2$ is a leaving group or $Y^1$ is a leaving group and $Y^2$ is amino. Suitable leaving groups are, for example, Cl, Br, I, alkylsulfonyloxy or arylsulfonyloxy.

Alkylations of this type are expediently carried out in water or an organic solvent such as a lower aliphatic alcohol (such as ethanol), benzyl alcohol, acetonitrile, nitromethane or glycol ether, at a temperature between −20° C. and the boiling point of the reaction mixture in the presence of a base such as an alkali metal hydroxide or an organic amine.

In addition, compounds of the formula IX can be condensed with compounds of the formula X.

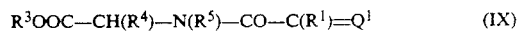

in which either $Q^1$ is amino + hydrogen and $Q^2$ is oxo or $Q^1$ is oxo and $Q^2$ is amino + hydrogen.

The condensation is expediently carried out in water or an organic solvent, such as a lower aliphatic alcohol, at a temperature between −20° C. and the boiling point of the reaction mixture in the presence of a reductant, such as $NaBH_3CN$, compounds of the formula I being obtained directly. However, Schiff's bases or enamines formed as intermediates can optionally also be reduced after prior isolation with the formation of compounds of the formula II, for example by hydrogenation in the presence of a transition metal catalyst.

Finally, the reaction of compounds of the formula IX ($Q^1 = H + NH_2$) with compounds of the formula XI or their reaction with compounds of the formulae XII and XIII expediently in the presence of a base, such as sodium alcoholate, in an organic solvent, such as a lower alcohol, at a temperature between −10° C. and the boiling point of the reaction mixture also leads to compounds of the formula II (n=2),

Schiff's bases formed intermediately as described above being reduced and a carbonyl group being converted into methylene by reduction (for example with a complex hydride).

In the abovementioned formulae V—XIII, R—$R^5$ and n are defined as in formula I. Protective groups introduced temporarily for the protection of reactive groups not involved in the reaction are removed after reaction is complete in a manner known per se (cf. Schröder, Lübke, loc cit., pages 1-75 and 247-270; Greene, "Protective Groups in Organic Synthesis", New York 1981).

Suitable calcium antagonists are the compounds of the formula II

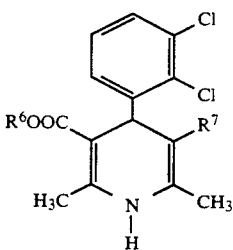

in which R[6] is methyl, ethyl or isopropyl and R[7] is methoxycarbonyl, ethoxycarbonyl or 1,2,4-oxadiazol-3-yl, and their physiologically tolerable salts.

Other suitable calcium antagonists are 5-[(3,4-dimethoxyphenylethyl)methylamino]-2-(3,4-dimethoxyphenyl)-2-isopropylvaleronitrile (verapamil),

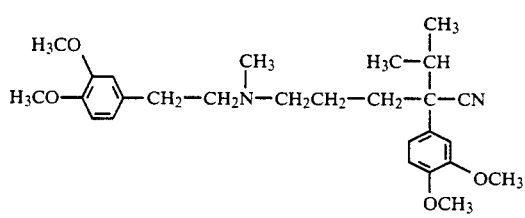

(2S-cis)-3-(acetoxy)-5-[2-dimethylamino)ethyl]-2,3-dihydroxy-2-(4-methoxyphenyl)-1,5-benzothiazepin-4(5H)-one (diltiazem),

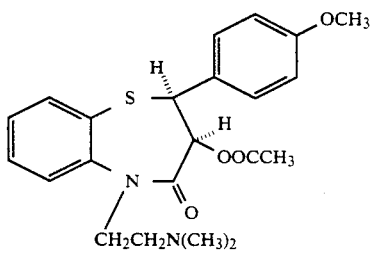

and dimethyl 1,4-dihydro-2,6-dimethyl-4-(2-nitrophenyl)-3,5-pyridinedicarboxylate (nifedipine).

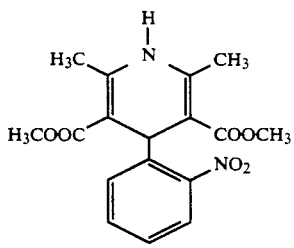

In addition to the three last-mentioned calcium antagonists, 4-(2,3-dichlorophenyl)-2,6-dimethyl-3-methoxycarbonyl-5-ethoxycarbonyl-1,4-dihydropyridine (felodipine) and 4-(2,3-dichlorophenyl)-2,6-dimethyl-3-(1,2,4-oxadiazol-3-yl) -5-isopropoxycarbonyl-1,4-dihydropyridine and their physiologically tolerable salts with acids are particularly preferred.

The following combinations are of very particular interest:

ramipril + felodipine or
ramipril + 4-(2,3-dichlorophenyl)-2,6-dimethyl-3-(1,2,4-oxadiazol-5-yl)-5-isopropoxycarbonyl-1,4-dihydropyridine or trandolapril + felodipine or trandolapril + 4-(2,3-dichlorophenyl)-2,6-dimethyl-3-(1,2,4-oxadiazol-3-yl) -5-isopropoxycarbonyl-1,4-dihydropyridine or trandolapril + verapamil or quinapril + felodipine or quinapril + 4-(2,3-dichlorophenyl)-2,6-dimethyl-3-(1,2,4-oxadiazol-5-yl) -5-isopropoxycarbonyl-1,4-dihydropyridine, and in each case the physiologically tolerable salts of said individual components if these form salts.

In addition to the use of said combinations, the invention also relates to the simultaneous, separate or periodic use of ACE inhibitors and calcium antagonists in the treatment of proteinuria.

The pharmaceutical preparations can be prepared, for example, either by intensively mixing the individual components as powders, or by dissolving the individual components in a suitable solvent such as, for example, a lower alcohol and then removing the solvent.

The ratio of the active compounds in the combinations and preparations according to the invention is preferably 1–15 parts by weight of ACE inhibitor to 15–1 parts by weight of calcium antagonist. The combinations and preparations according to the invention contain a total of preferably 0.5–99.5% by weight, in particular 4–96% by weight, of these active compounds.

For the use according to the invention in mammals, preferably in the human, the doses of an ACE inhibitor of the abovementioned formula vary, for example, in the range from 0.05 to 100 mg/kg/day and those of a calcium antagonist in the range from 0.05 to 200 mg/kg/day.

The preparations or products according to the invention can be administered parenterally or orally. The oral form of administration is preferred.

The pharmacologically utilizable combinations of the present invention and their salts can be used for the production of pharmaceutical preparations which contain an effective amount of the active substances together with excipients and which are suitable for enteral and parenteral administration. Tablets or gelatin capsules are preferably used which contain the active compounds together with diluents, for example lactose, dextrose, cane sugar, mannitol, sorbitol, cellulose and/or glycerin and lubricants such as silica, talc, stearic acid or their salts, such as magnesium stearate or calcium stearate, and/or polyethylene glycol. Tablets also contain binders such as magnesium aluminum silicate, starch, gelatin, tragacanth, methylcellulose, sodium carboxymethylcellulose and/or polyvinylpyrrolidone and, if required, colorant, flavorings and sweeteners.

Injectable solutions are preferably isotonic aqueous solutions or suspensions which can be sterilized.

Suitable salts of the abovementioned compounds are, depending on the acidic or basic nature of these compounds, alkali metal or alkaline earth metal salts or salts with physiologically tolerable amines or salts with inorganic or organic acids such as, for example, HCl, HBr, $H_2SO_4$, maleic acid, fumaric acid, tartaric acid and citric acid.

Prevention of progressive proteinuria in rats having a residual kidney

1. METHOD

⅔ of the right kidney of adult male Sprague-Dawley rats was first infarcted by a ligature and the contralateral kidney was removed after an interval of 1 week. The animals then immediately received the medication with the feed over a period of 8 weeks. The feed consumption showed that group II (n:17) had been treated with 58 mg/ kg of felodipine (FE), group III (n:10) had been treated with 1.6 mg/kg of ramipril (RA) and group IV (n:11) had been treated with 41 mg/kg of FE and 1.4 mg/kg of RA. The control group I received normal feed. The urine was in each case collected over a period of 24 hours before the operations and after 1, 3, 5 and 7 weeks. Blood samples were drawn from the retroorbital plexus under light pentobarbital anesthesia, in each case on the day before and at the end of the study after the measurement of blood pressure in the carotid artery under terminal pentobarbital anesthesia.

2. RESULTS

The mean arterial blood pressure was $160\pm7$ mm Hg in control group I, $122\pm3$ mm Hg under FE, $117\pm7$ mm Hg under RA and $108\pm4$ mm Hg under FE and RA. The protein-uria which was less than 20 mg/24 h before the operation, increased in the control group continuously up to $105\pm28$ mg/24 h in the 7th week. The increase of proteinuria was delayed by 2 weeks under FE, but finally reached similar values at $114\pm28$ mg/24 h. The excretion of protein under RA was clearly lower at $48\pm15$ mg/24 h. It was reduced again to only $31\pm4$ mg/24 h under RA plus FE. The plasma creatinine level doubled after the operation in all groups by on average 42 to 73 mol/l, but was then not further affected by the medication. The plasma CE activity was reduced under RA with and without FE by on average 80% while FE alone had no effect.

In FIGS. 1 and 2, T is the test period in weeks; the values on the left without a number are before the operation. The values denoted by A in FIGS. 1-4 are after the administration of 58 mg/kg of felodipine, those by B after administration of 1.6 mg/kg of ramipril and those by C after administration of a combination of 1.4 mg of ramipril and 41 mg of felodipine. D is the control.

3. DISCUSSION

Figure 1:
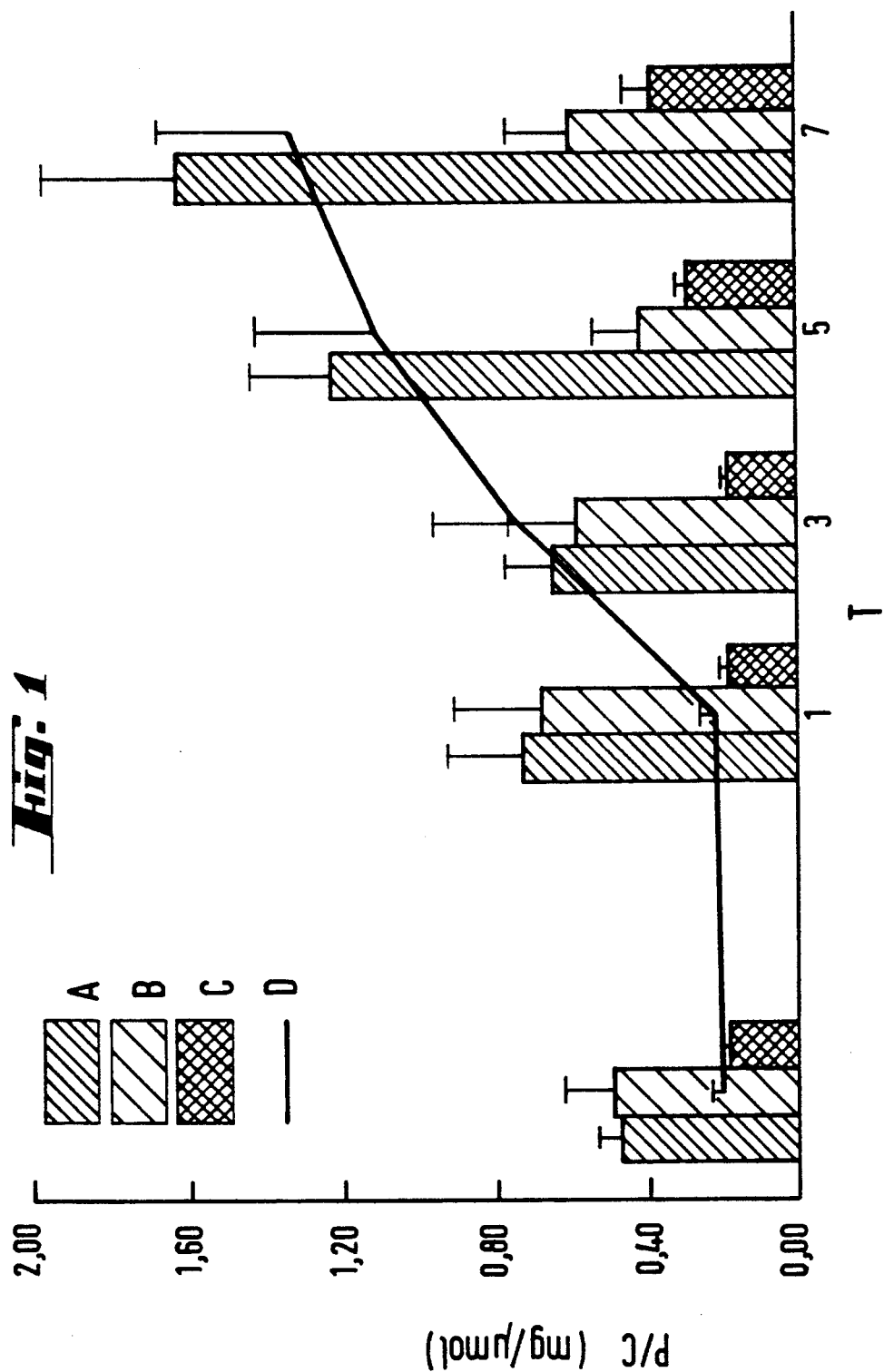
FIG. 1 shows the ratio of protein excretion and creatinine excretion P/C in mg/μmol.
Figure 2:
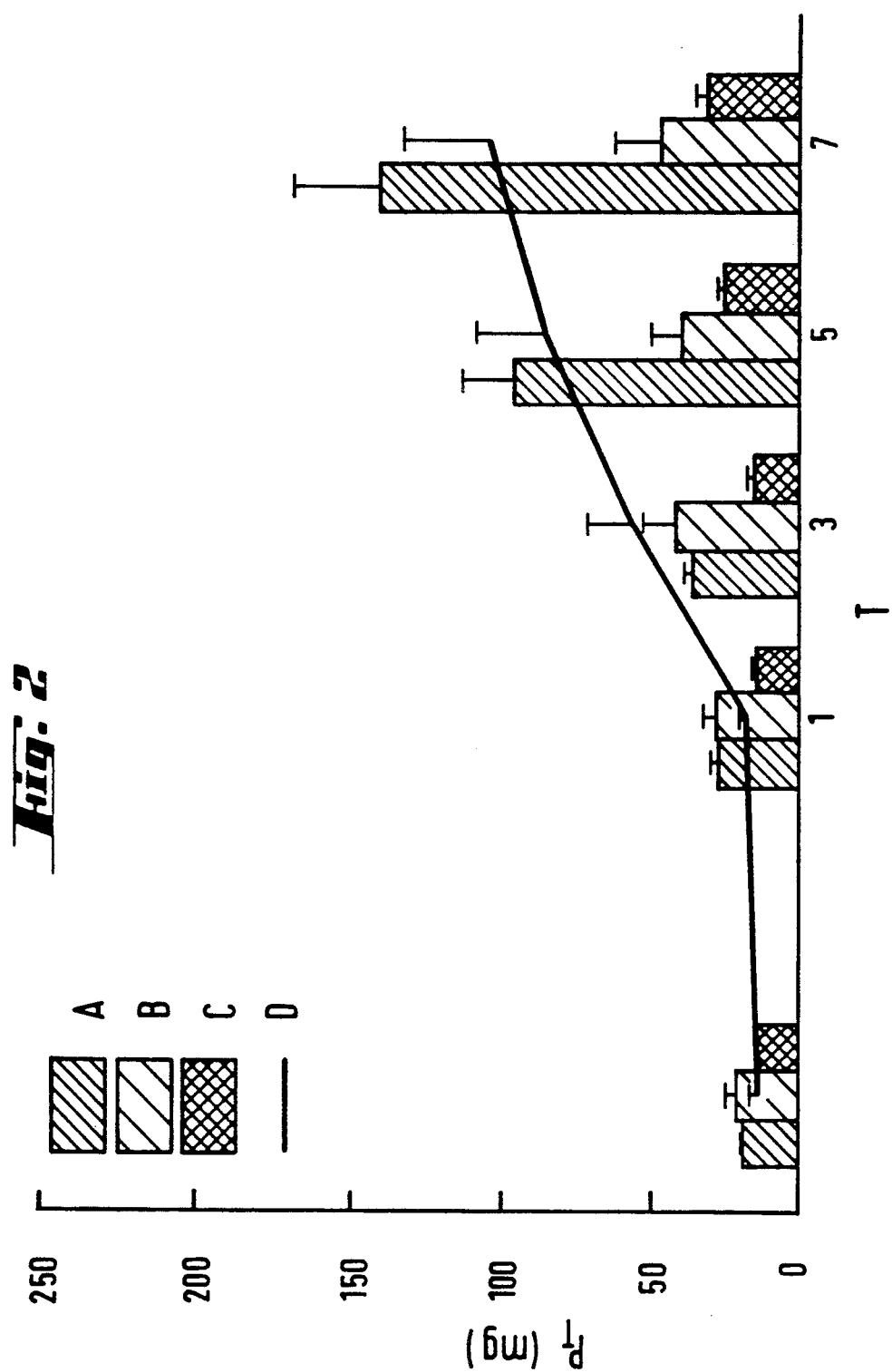
FIG. 2 shows the total protein excretion $P_T$ (mg) in the course of 24 hours.
Figure 3:
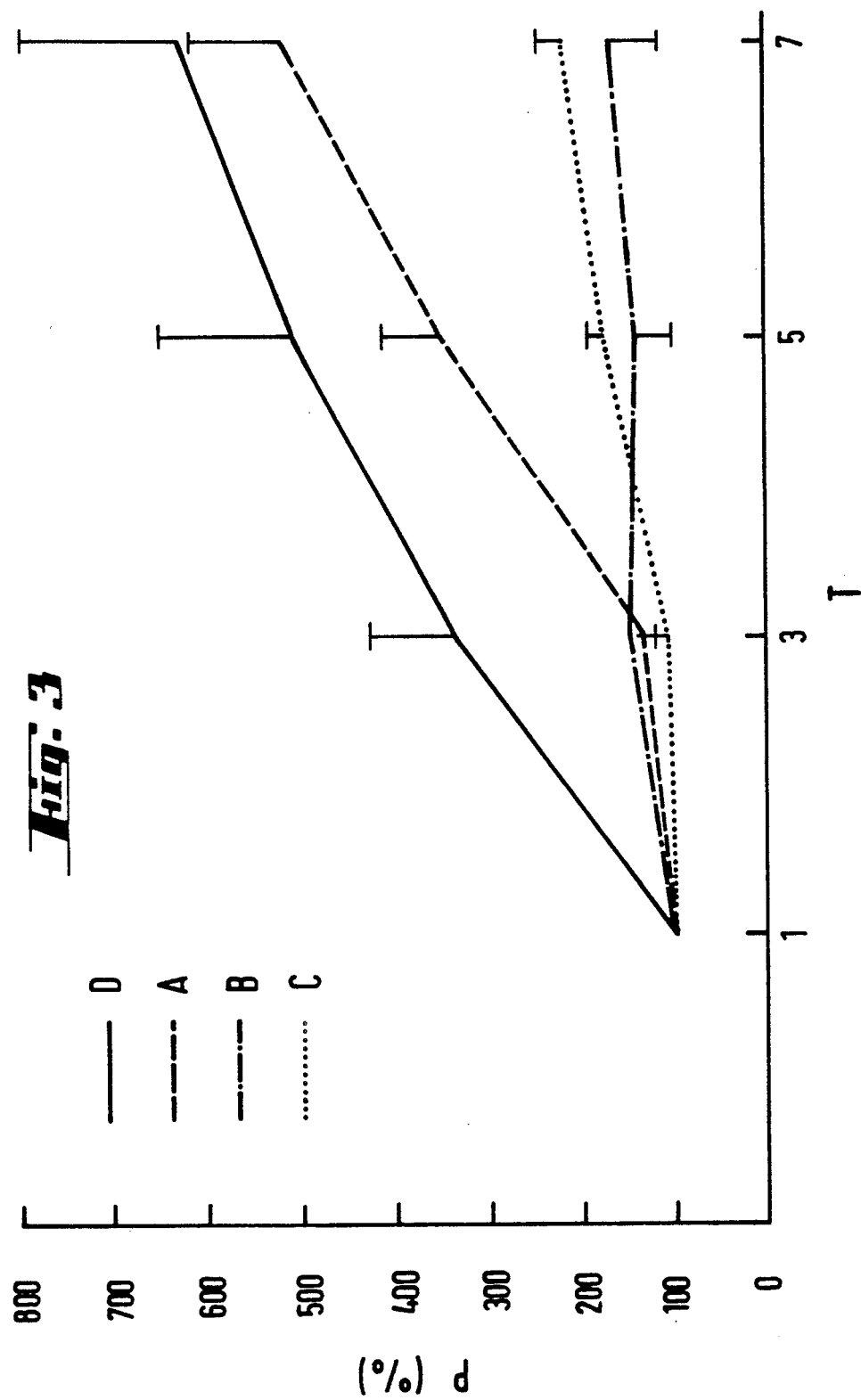
FIG. 3 is the percentage protein excretion %P in the course of 24 hours plotted against the test period T.
Figure 4:
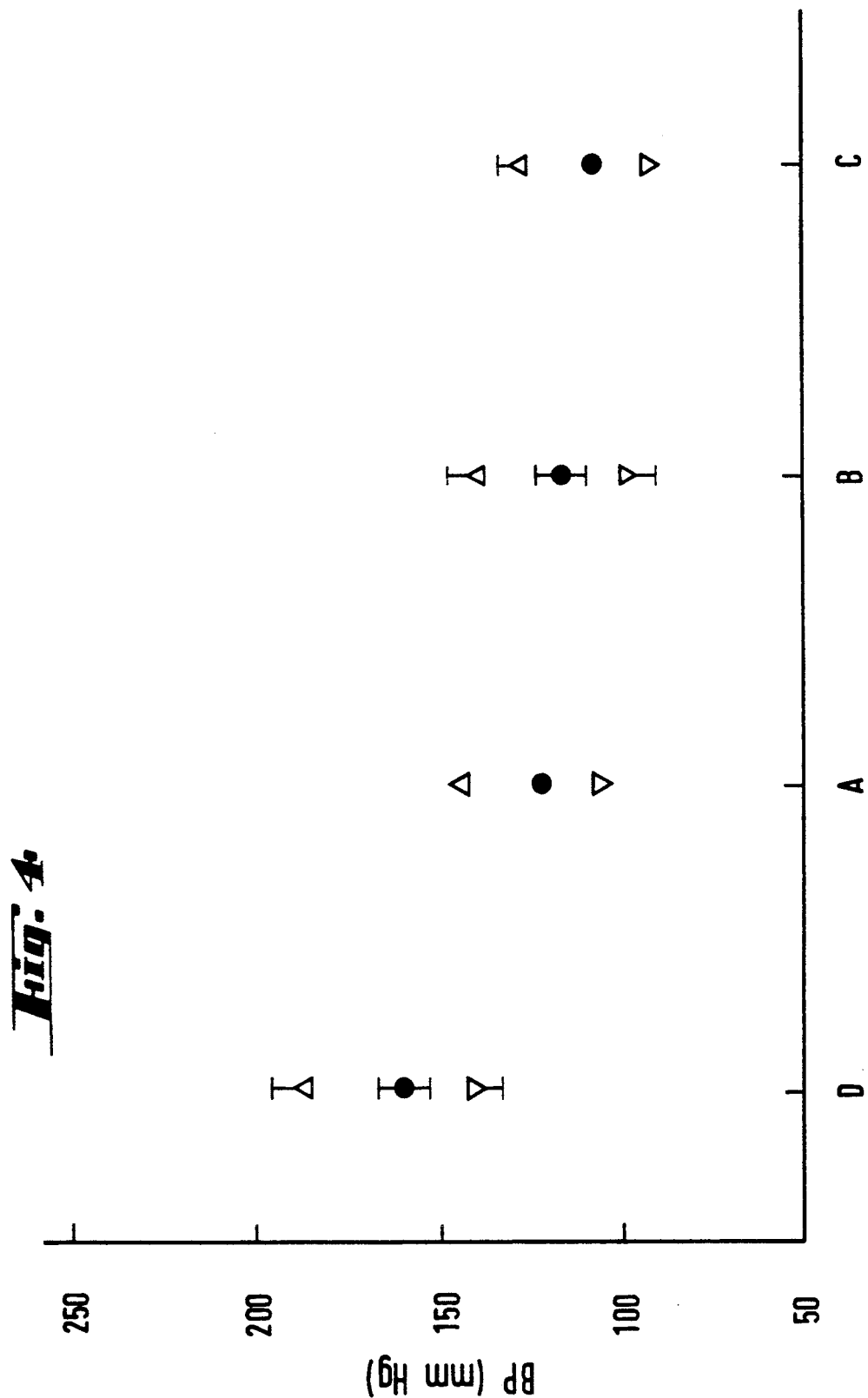
FIG. 4 shows the blood pressure BP (mm Hg), where · is the mean blood pressure, Δ is the systolic blood pressure and ∇ is the diastolic blood pressure.

Results of tests using rats confirm that calcium antagonists and ACE inhibitors, in spite of the same action on the systemic blood pressure, diverge in their action on the impairment of renal function caused by loss of nephrons.

The investigation further showed that control of the systemic blood pressure with a calcium antagonist indeed delayed the start of proteinuria, but finally rather caused an acceleration of the loss of renal function. This unfavorable development could be abolished by simultaneous administration of an ACE inhibitor.

The following examples are used to illustrate the present invention without it being limited thereto:

EXAMPLE 1

Production of an oral combination preparation from ramipril and felodipin 1000 tablets, which contain 2 mg of ramipril and 6 mg of felodipine, are prepared as follows:
ramipril 2 g
felodipine 6 g
maize starch 140 g
gelatin 7.5 g
microcrystalline cellulose 2.5 g
magnesium stearate 2.5 g The two active compounds are mixed with an aqueous gelatin solution. The mixture is dried and ground to give granules. Microcrystalline cellulose and magnesium stearate are mixed with the granules. The granules thus prepared are compressed to give 1000 tablets, each tablet containing 2 mg of ramipril and 6 mg of felodipine.

EXAMPLE 2

Production of an Oral Combination Preparation from Trandolapril and Verapamil 1000 tablets, which contain 3 mg of trandolapril and 50 mg of verapamil, are prepared as follows:
trandolapril 3 g
verapamil 50 g
maize starch 130 g
gelatin 8.0 g
microcrystalline cellulose 2.0 g
magnesium stearate 2.0 g The two active compounds are mixed with an aqueous gelatin solution. The mixture is dried and ground to give granules. Microcrystalline cellulose and magnesium stearate are mixed with the granules. The granules thus prepared are compressed to give 1000 tablets, each tablet containing 3 mg of trandolapril and 50 mg of verapamil.

EXAMPLE 3

Production of an Oral Combination Preparation from Quinapril and Felodipine 1000 tablets, which contain 2.5 mg of quinapril and 6 mg of felodipine, are prepared as follows:
quinapril 2.5 g
felodipine 5 g
maize starch 150 g
gelatin 7.5 g
microcrystalline cellulose 2.5 g
magnesium stearate 2.5 g The two active compounds are mixed with an aqueous gelatin solution. The mixture is dried and ground to give granules. Microcrystalline cellulose and magnesium stearate are mixed with the granules. The granules thus prepared are compressed to give 1000 tablets, each tablet containing 2.5 mg of quinapril and 5 mg of felodipine.

We claim:

1. A method for the prevention and/or treatment of proteinuria comprising the step of administering to a mammal in need thereof (a) an ACE inhibitor of formula I

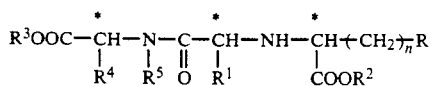
(I)

wherein n is 1 or 2,

R is $(C_1-C_6)$-alkyl or $(C_6-C_{12})$-aryl, $R^1$ is hydrogen or $(C_1-C_6)$-alkyl which may be optionally substituted by an amino group, $R^2$ and $R^3$ can be identical or different and are selected from hydrogen, $(C_1-C_6)$-alkyl, and $(C_6-C_{12})$-aryl-$(C_1-C_4)$-alkyl, and $R^4$ and $R^5$, together with the atoms carrying them, form a ring system selected from tetrahydroisoquinoline, decahydroisoquinoline, octahydroindole, and octahydrocyclopenta[b]pyrrole, or a physiologically tolerable salt thereof; and (b) a calcium antagonist of formula II

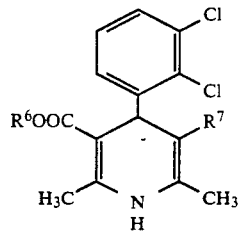
(II)

wherein $R^6$ is methyl, ethyl or isopropyl, and $R^7$ is methoxycarbonyl, ethoxycarbonyl or 1,2,4-oxadiazol-3-yl, or a physiologically tolerable salt thereof;

wherein said ACE inhibitor and said calcium antagonist are administered in an amount effective to prevent or treat proteinuria and its symptoms.

2. The method of claim 1 wherein said ACE inhibitor is 2-[N-(1-S-ethoxycarbonyl-3-phenylpropyl)-S-alanyl](1S,3S,5S)-2-azabicyclo[3.3.0]octane-3-carboxylic acid or a physiologically tolerable salt thereof.

3. The method of claim 1 wherein said ACE inhibitor is 1-[N-(1-S-ethoxycarbonyl-3-phenylpropyl)-S-alanyl]-(2S,3aR,7aS)-octahydro[1H]indole-2-carboxylic acid or a physiologically tolerable salt thereof.

4. The method of claim 1 wherein said ACE inhibitor is 2[N-(1-S-ethoxycarbonyl-3-phenylpropyl)-S-alanyl]-1,2,3,4-tetrahydroquinoline-3-S-carboxylic acid or a physiologically tolerable salt thereof.

* * * * *